(12) United States Patent
Narayanan et al.

(10) Patent No.: US 6,197,098 B1
(45) Date of Patent: Mar. 6, 2001

(54) FAST DRYING BIOCIDAL PRESERVATIVE COMPOSITION

(75) Inventors: Kolazi S. Narayanan, Wayne, NJ (US); Domingo I. Jon, New York, NY (US); Donald Prettypaul, Englewood, NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/464,758

(22) Filed: Dec. 16, 1999

(51) Int. Cl.$^7$ .......................... A01N 25/00; A01N 31/00; A01N 33/00; A01N 43/36
(52) U.S. Cl. .................... 106/18.32; 106/18.33; 106/18.34; 252/8.57; 514/341; 514/343; 514/634
(58) Field of Search ................ 106/18.32, 18.33, 106/18.34; 252/8.57; 514/341, 343, 634

(56) References Cited

U.S. PATENT DOCUMENTS 5,071,463 * 12/1991 Narayanan et al. .................. 504/116
5,262,414 * 11/1993 Albert et al. ...................... 514/237.5

FOREIGN PATENT DOCUMENTS

| 351 195 | * | 1/1990 | (EP) . |
| 2 118 160 | * | 10/1983 | (GB) . |
| 351 195 | * | 1/1997 | (JP) . |
| 99/55505 | * | 11/1999 | (WO) . |

* cited by examiner

Primary Examiner—Anthony Green
(74) Attorney, Agent, or Firm—Marilyn J. Maue; William J. Davis; Walter Katz

(57) ABSTRACT

The invention relates to a fast drying biocidal composition having enhanced penetration for the treatment and preservation of wood, leather and similar natural products which comprises:

A. between about 10 and about 50 wt. % of a concentrate comprising a petroleum distillate boiling above 40° C. and containing
  (a) between about 0.5 and about 7 wt. % of an active nitrogen- or sulfur-containing biocide and
  (b) between about 20 and about 55 wt. % of a solvent for said active biocide selected from the group consisting of
    (i) butyrolactone containing 0 to 85 wt. % N-methyl pyrrolidone and/or 0 to 85 wt. % of a $C_2$ to $C_4$ aliphatic alcohol and
    (ii) N-methyl pyrrolidone containing 0 to 85 wt. % of a $C_2$ to $C_4$ alcohol and
B. from about 90 to about 50 wt. % of a $C_2$ to $C_4$ aliphatic alcohol containing 0 to 85 wt. % of mineral spirit as a diluent to provide a sprayable composition and to the process for treating a wood or leather substrate with said biocidal composition.

6 Claims, No Drawings

FAST DRYING BIOCIDAL PRESERVATIVE COMPOSITION

BACKGROUND OF THE INVENTION

In one aspect the invention relates to concentrate compositions for non-specific, i.e. gram-negative and gram positive, fungicides and insecticides. In another aspect the invention is directed to fast drying, deeply penetrating, diluted concentrate compositions useful in the preservation of wood and leather goods.

Current wood and leather preservatives containing water insoluble active agents generally employ inexpensive solvents or diluents such as white spirit, petroleum naphtha and the like, having high aromatic content. However, these compositions do not have good penetrating properties and are relatively slow drying. Further, these compositions tend to be physically unstable and separate into two phases resulting in undesirable residues and darkened coating of the substrate. It has also been reported that the current preservatives do not achieve uniform distribution of the active component due to phase separation so that accurate concentrations and dosages are difficult to administer.

Accordingly, it is a purpose of this invention to overcome the above shortcomings by providing commercially feasible and economical, homogeneous biocidal compositions suitable for the preservation of wood, leather and other articles of manufacture.

SUMMARY OF THE INVENTION

In accordance with this invention there is provided a biocidal concentrate comprising:
(a) between about 0.5 to about 7 wt. % of an active biocidal nitrogen-containing and/or sulfur-containing component and
(b) between about 20 and about 55 wt. % of a component selected from the group consisting essentially of (i) butyrolactone containing 0 to about 85 wt. % N-methyl pyrrolidone and/or 0 to about 80 wt. % of a $C_2$ to $C_4$ aliphatic alcohol and (ii) about a 10/90 to 60/40 mixture of N-methyl pyrrolidone/$C_2$ to $C_4$ aliphatic alcohol.

Although the above concentrate can be directly incorporated inweto a commercial matrix or premixed formulation, it is generally desirable to dilute the concentrate by between about 0.5 and about 80 volumes, preferably 10 to 60 volumes, with a diluent comprising a petroleum distillate boiling above 40° C., a $C_2$ to $C_4$ alcohol or a mixture thereof to provide a composition having an active content of from about 2 ppm to about 5% and a total $C_2$ to $C_4$ aliphatic alcohol content of between about 20 and about 90 wt. %. This composition is then applied directly to the substrate or may be combined with conventional preservative excipients and coated or sprayed on the substrate.

DETAILED DESCRIPTION OF THE INVENTION

The active component in the above concentrate is a conventional water insoluble, fungicidal or insecticidal nitrogen- and/or sulfur-containing compound. Representative examples of these include imide, amide, amine, azo, thio, imidiazole and halogenated compounds of which [1-(6-chloro-3-pyridylmethyl-N-nitroimidazolidin-2-ylideneamine] (Imidacloprid); [N,N-(1,4-piperazine diyl formamide] (Triforine); guanidine; dodecyl guanidine acetate (Dodine acetate); iminoctadine; nicotine and salicylate, sulfate, tartrate, and fluoro and chloro salts thereof; 5-ethoxy-3-trichloromethyl-1,2,4-thiadiazole (Etridiazol); 2-(4-thiazonyl) benzimidazole (Thiabendazole), 1-(2-[2,4-dichlorophenyl]-4-propyl-1,3-dioxolan-2-ylmethyl)-1H-1,2,4-triazole (Propiconazole); O,O-diethyl-O-quinoxalin-2-yl phosphorothioate (Quinalphos); N-(trichlorpmethylthio)-4-cyclohexene-1.2-dicarboximide (Captan); N-(trichloromethylthio) phthalimide (Folpet) and (RS)-2,4-difluoro-α-(1H-1,2,4-triazol-1-yl methyl) benzhydryl alcohol (Flutriafol) are examples. Generally the conventional dosages of these biocides are recommended for the diluted compositions of this invention.

Although methanol, ethanol, n-propanol, isopropanol, n-, iso- or tert-butanol or a combination of these can be used in the above concentrate or diluent composition, isopropanol is preferred to further enhance uniform active distribution and fast drying properties. The weight ratio of active component to $C_2$ to $C_4$ alcohol in the final composition is generally between about 1:70 and about 1:5,000 depending on the toxicity and efficacy of the biocidally active compound.

In the above concentrate, butyrolactone, when used alone or in combination with N-methyl pyrrolidone, provides better distribution of the active component on the site of application than N-methyl pyrrolidone alone and therefor, at least 0.5 wt. % of the lactone is preferred in the concentrate solution. The N-methyl pyrrolidone in the concentrate may be augmented with a higher alkyl pyrrolidone such as a $C_8$ to $C_{12}$ alkyl pyrrolidone, preferably N-octyl pyrrolidone, to provide enhanced spreadability and substrate penetration. However, the concentration of the higher alkyl pyrrolidone with respect to N-methyl pyrrolidone should not exceed 10 wt. %.

Petroleum diluents such as white spirit, petroleum ether or other petroleum distillates boiling above 40° C., preferably above 60° C., are employed from a cost consideration; however, at least a 20 wt. % concentration of $C_2$ to $C_4$ alcohol in the overall final composition is needed to prevent phase separation. Additionally, the combination of such distillates with the $C_2$ to $C_4$ alcohol greatly improves the penetration of the preservative into the pores of the substrate thus extending the degree of protection while providing more uniform distribution of the active component in the resulting homogeneous composition. Thus, accurate dosages of the biocide can be predetermined and administered. The presence of the alcohol reduces undesirable residue in and on the substrate in proportion to its concentration. Other benefits, such as reduced toxicity resulting from extended human exposure and extension of storage capability for the diluted concentrate, are also realized by the use of the present composition. Finally, it is discovered that the use of isopropyl alcohol permits at least 50% increase in loading of the active component as compared to a composition employing petroleum diluent alone.

The preferred composition applied in effective amount to the wood or leather substrate of this invention comprises:
A. between about 10 and about 50 wt. % of a concentrate comprising a petroleum distillate boiling above 40° C. and containing
  (a) between about 0.5 and about 7 wt. % of an active nitrogen- or sulfur-containing biocide and
  (b) between about 20 and about 55 wt. % of a solvent for said active biocide selected from the group consisting of
    (i) butyrolactone containing 0 to 85 wt. % N-methyl pyrrolidone and/or 0 to 85 wt. % of a $C_2$ to $C_4$ aliphatic alcohol and
    (ii) N-methyl pyrrolidone containing 0 to 85 wt. % of a $C_2$ to $C_4$ alcohol and
B. from about 90 to about 50 wt. % of a $C_2$ to $C_4$ aliphatic alcohol containing 0 to 85 wt. % of mineral spirit as a diluent to provide a sprayable composition.

Having generally described the invention, reference is now had to the accompanying examples which are provided to illustrate preferred and comparative embodiments concerning the invention. However, these examples are not to be construed as limiting to the scope of the invention as more broadly defined in the appended claims.

EXAMPLES 1–5

The following concentrates, shown in Table A, were prepared by mixing imidacloprid with the selected solvent in a 100 ml beaker, at a temperature of 25° C. and agitating until a uniform mixture was obtained. The resulting concentrate solutions were then diluted as reported in Table B.

TABLE A

| CONCENTRATE | EXAMPLES (parts by weight) | | | | |
| --- | --- | --- | --- | --- | --- |
| | 1 | 2 | 3 | 4 | 5 |
| BLO[1] | 0 | 43.24 | 43.24 | 30.02 | 0 |
| Agsol Ex 1[2] | 48.78 | 0 | 0 | 0 | 49.38 |
| Shellsol AB[3] | 48.78 | 54.06 | 54.06 | 37.54 | 49.38 |
| Imidacloprid | 2.44 | 2.7 | 2.7 | 1.88 | 1.24 |
| Isopropyl alcohol | 0 | 0 | 0 | 30.56 | 0 |
| DILUENT | | | | | |
| Concentrate | 20.5 | 18.5 | 18.5 | 26.6 | 40.0 |
| White Spirit | 0 | 0 | 73.4 | 73.4 | 60.0 |
| Isopropyl alcohol | 79.5 | 81.5 | 12.1 | 0 | 0 |

[1]butyrolactone
[2]N-methyl pyrrolidone
[3]Petroleum distillate containing aromatic compounds (b.p. > 60° C.)

TABLE B

| Diluted Concentrate of Example | 1 | 2 | 3 | 4 | 5 |
| --- | --- | --- | --- | --- | --- |
| Initial observation | clear | clear | cloudy | cloudy | cloudy |
| After 0.5 hour | clear | clear | 2 phases | 2 phases | 2 phases |
| After 2 weeks | clear | clear | 2 phases | 2 phases | 2 phases |

About 10 g. of each of the products of the diluted concentrate of Examples 1–5, as reported in TABLE A, were then uniformly sprayed onto individual surfaces of untreated 2×4×24 inch pine wood samples. These samples together with an untreated pine wood sample were placed in the soil of an outdoor plot. After several days, the wood samples were compared and the results of these tests are reported in following Table C.

TABLE C

| Wood Samples Treated With Diluted Concentrates of Examples | Insect Control |
| --- | --- |
| 1 | excellent |
| 2 | excellent |
| 3 | good |
| 4 | good |
| 5 | minor |
| Untreated | none |

The above test with the diluted concentrate of Example 5 indicates that, when butyrolactone is omitted in the concentrate formulation, a mixture of N-methyl pyrrolidone and $C_2$ to $C_4$ alkanol is required in the diluted product composition in order to achieve adequate insect control.

When the diluent mixture of 25 parts isopropyl alcohol and 53 parts white spirit is substituted for the diluent mixture employed in example 3, the diluted concentrate remains clear.

Optionally, up to about 4.5 wt. % wood vinegar can be added to the concentrate as a buffer to stabilize any tendency of the active ingredient toward hydrolysis.

It will become apparent to the skilled artisan that various modifications and substitutions in the above examples, within the parameters of this disclosure, can be made without departing from the scope of this invention and that various excipients can be added to the above formulations.

What is claimed is:

1. The process for preserving wood or leather by applying to a wood or leather substrate an effective fungicidal/insecticidal amount of a composition comprising A. between about 10 and about 50 wt. % of a concentrate comprising a petroleum distillate boiling above 40° C. and containing
      (a) between about 0.5 and about 7 wt. % of an active nitrogen- or sulfur-containing biocide and
      (b) between about 20 and about 55 wt. % of a solvent for said active biocide selected from the group consisting of
         (i) butyrolactone containing 0 to 85 wt. % N-methyl pyrrolidone and/or 0 to 85 wt. % of a $C_2$ to $C_4$ aliphatic alcohol and
         (ii) N-methyl pyrrolidone containing 0 to 85 wt. % of a $C_2$ to $C_4$ alcohol and
   B. from about 90 to about 50 wt. % of a $C_2$ to $C_4$ aliphatic alcohol containing 0 to 85 wt. % of mineral spirit as a diluent to provide a sprayable composition.

2. The process of claim 1 wherein the $C_2$ to $C_4$ alcohol of B contains not more than 75% mineral spirit.

3. The process of claim 1 wherein said alcohol is isopropyl alcohol.

4. The process of claim 1 wherein the diluent additionally contains a minor amount of wood vinegar (pyroligneous acid).

5. The process of claim 1 wherein said petroleum distillate boils above 60° C.

6. The process of claim 1 wherein said biocide is selected from the group consisting of an imidacloprid, a guanidine and nicotine and salicylate, sulfate, tartrate, fluoride and chloride salts of said biocides.

* * * * *